US010517645B2

(12) United States Patent
van der Pol

(10) Patent No.: US 10,517,645 B2
(45) Date of Patent: Dec. 31, 2019

(54) PEDICLE SCREW WITH TULIP

(71) Applicant: Signus Medizintechnik GmbH, Alzenau (DE)

(72) Inventor: Bas van der Pol, Alzenau (DE)

(73) Assignee: Signus Medizintechnik GmbH, Alzenau (DE)

( * ) Notice: Subject to any disclaimer, the term of this patent is extended or adjusted under 35 U.S.C. 154(b) by 213 days.

(21) Appl. No.: 15/174,814

(22) Filed: Jun. 6, 2016

(65) Prior Publication Data

US 2016/0361096 A1 Dec. 15, 2016

(30) Foreign Application Priority Data

Jun. 9, 2015 (DE) .................. 10 2015 007 467
Jun. 23, 2015 (DE) .................. 10 2015 008 036

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/7076* (2013.01); *A61B 17/863* (2013.01); *A61B 17/864* (2013.01); *A61B 17/7098* (2013.01)

(58) Field of Classification Search
CPC .............. A61B 17/7076; A61B 17/7032–7046
See application file for complete search history.

(56) References Cited

U.S. PATENT DOCUMENTS

| 8,361,122 | B2 | 1/2013 | Barrus et al. | |
|---|---|---|---|---|
| 9,247,967 | B2 * | 2/2016 | Wilcox | ............. A61B 17/7037 |
| 9,439,681 | B2 * | 9/2016 | Keyer | ................ A61B 17/7037 |
| 10,039,572 | B2 * | 8/2018 | Harris | ................ A61B 17/7037 |

(Continued)

*Primary Examiner* — Jacqueline T Johanas
(74) *Attorney, Agent, or Firm* — Schwabe, Williamson & Wyatt, P.C.

(57) ABSTRACT

An instrument set (1) for connecting vertebral bodies, comprising a screw (10) which has a screw head (12) and a shaft (14) and can be screwed into a pedicle, a head piece (2) which can be connected polyaxially to the screw (10) for coupling to a rod system (100) and which has a sleeve-shaped tulip (20) having a first insertion opening (21) for insertion of the screw head (12) in an insertion direction (E), and a tool (40), is developed according to the invention in that the head piece (2) has a saddle (30) in the interior region (22) of the tulip (20), the saddle (30) has a receiving region (32) for receiving the screw head (12) in a first end region (31a) that faces the first insertion opening (21a) and a coupling region (35) that can be coupled to the tool (40) in a second end region (31b) opposite the receiving region (32), and the saddle can be moved between a released position (23a), which can be reached by inserting the screw head (12), and a locked position (23b), which can be reached by moving the screw head (12) out of the released position (23a) in the direction opposite the insertion direction (E), wherein in the locked position (23b), the screw head (12) held in the receiving region (32) cannot be disengaged from the receiving region (32), and the saddle (30) can be fixed in a released position (23a) that enables the release of the screw head (12) from the receiving region (32) by means of the tool (40), which is coupled to the coupling region (35).

26 Claims, 14 Drawing Sheets

(56) References Cited

U.S. PATENT DOCUMENTS

| | | | |
|---|---|---|---|
| 2004/0138662 A1* | 7/2004 | Landry | A61B 17/1604 606/86 A |
| 2010/0234902 A1* | 9/2010 | Biedermann | A61B 17/7032 606/305 |
| 2011/0098755 A1* | 4/2011 | Jackson | A61B 17/7008 606/305 |
| 2011/0152949 A1* | 6/2011 | Biedermann | A61B 17/7037 606/305 |
| 2011/0160779 A1* | 6/2011 | Schlaepfer | A61B 17/7032 606/305 |
| 2011/0288599 A1 | 11/2011 | Michielli et al. | |
| 2012/0041490 A1* | 2/2012 | Jacob | A61B 17/7032 606/264 |
| 2012/0059426 A1* | 3/2012 | Jackson | A61B 17/7008 606/300 |
| 2012/0116464 A1* | 5/2012 | Denis | A61B 17/7032 606/308 |
| 2012/0143266 A1* | 6/2012 | Jackson | A61B 17/7008 606/328 |
| 2014/0107708 A1* | 4/2014 | Biedermann | A61B 17/7082 606/278 |
| 2014/0142632 A1* | 5/2014 | Keyer | A61B 17/7037 606/265 |
| 2014/0163619 A1* | 6/2014 | Harvey | A61B 17/7032 606/278 |
| 2014/0236239 A1* | 8/2014 | Biedermann | A61B 17/7037 606/278 |
| 2014/0249532 A1* | 9/2014 | Biedermann | A61B 17/1671 606/80 |
| 2014/0277159 A1* | 9/2014 | Spratt | A61B 17/7037 606/278 |
| 2015/0080960 A1* | 3/2015 | Biedermann | A61B 17/7037 606/278 |
| 2015/0148848 A1* | 5/2015 | Doubler | A61B 17/704 606/278 |
| 2015/0223844 A1* | 8/2015 | Leff | A61B 17/705 606/265 |
| 2016/0262816 A1* | 9/2016 | Doubler | A61B 17/8605 |

\* cited by examiner

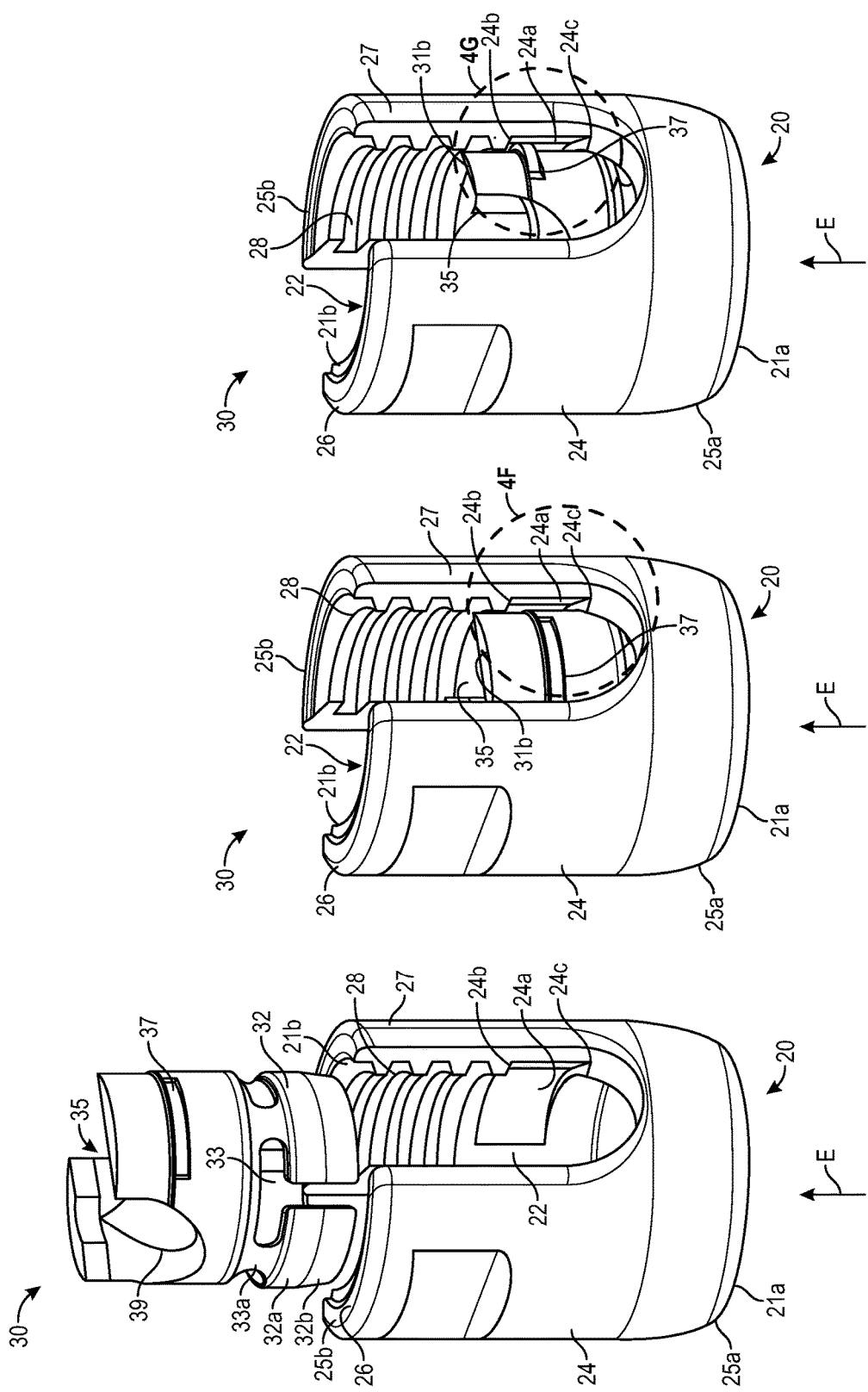

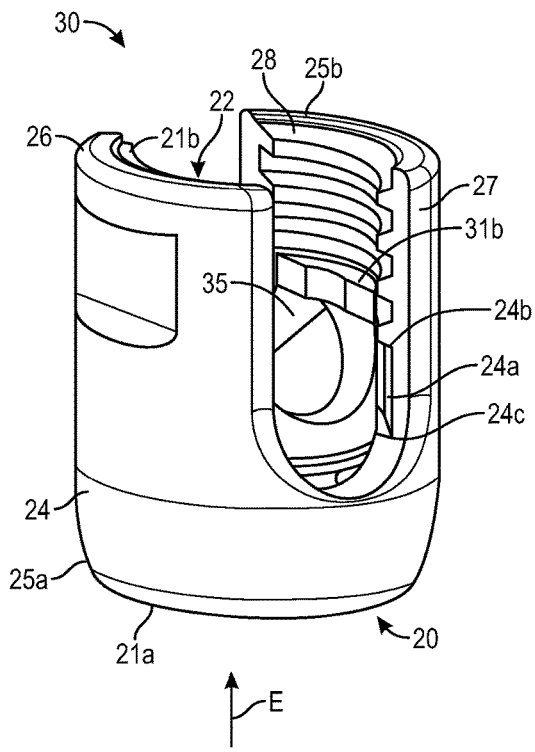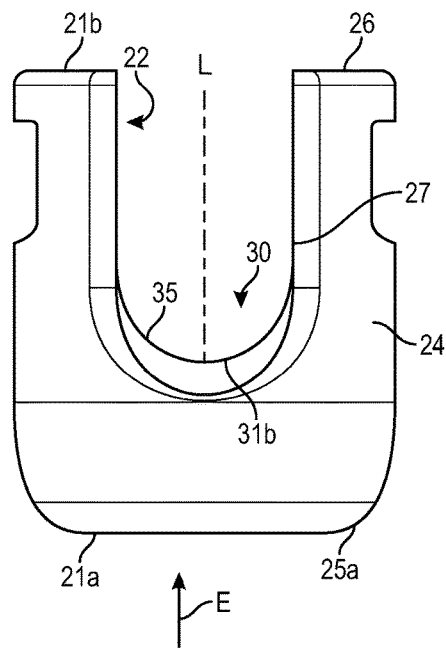
FIG. 4D  FIG. 4E
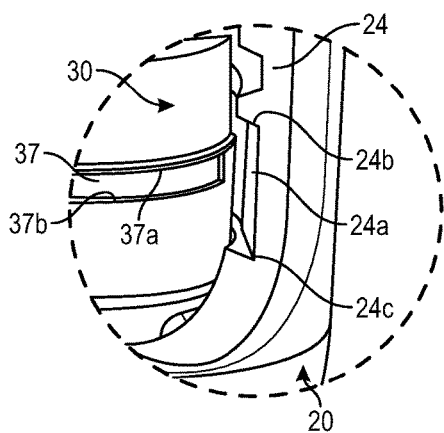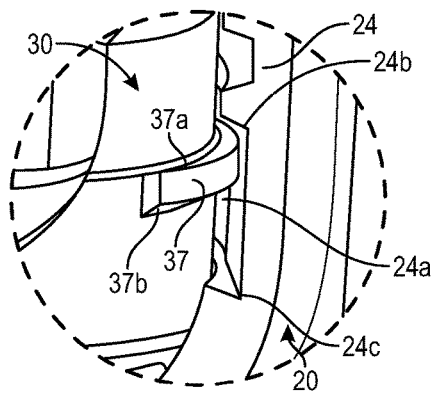
FIG. 4F  FIG. 4G

PEDICLE SCREW WITH TULIP

CROSS REFERENCE TO RELATED APPLICATIONS

The present application claims international priority under 35 U.S.C. § 119 to co-pending German Patent Application No. 102015008036.9, filed 23 Jun. 2015, and German Patent Application No. 102015007467.9, filed 9 Jun. 2015, the entire content and disclosure of which is hereby incorporated by reference in its entirety.

BACKGROUND

The invention relates to an instrument set for connecting vertebral bodies, comprising a screw which can be screwed into a pedicle and which has a screw head and a shaft, a head piece designed for coupling to a system of rods, which can be connected polyaxially to the screw and which has a sleeve-shaped tulip having a first insertion opening for insertion of the screw head in an insertion direction, and a tool.

An instrument set of this type is known from the prior art and is used, for example, in spinal surgeries for stabilizing or correcting the spinal column. In such surgeries, screw shafts are first screwed into the pedicles of adjoining vertebral bodies to be connected to one another. The head of each screw can be connected to one head piece. A typically rigid connecting rod is then coupled to head pieces of the screws longitudinally such that the vertebrae are held in the desired position by the rod.

In such a surgical procedure, the coupling of the rigid connecting rod to the head pieces presents a challenge. It is known from the prior art that so-called polyaxial screws simplify this step of the surgical procedure substantially. A polyaxial screw consisting of a screw and a head piece connected to the screw enables the shaft of the screw to pivot in relation to the longitudinal axis of the head piece within a certain range. The head piece is also capable of rotating around its longitudinal axis with the shaft in any pivot position. Inserting the connecting rod into head pieces that can move relative to the shaft of the screw is much easier than inserting the connecting rod into head pieces that are rigidly connected to the shaft of the screw. Moreover, a head piece that is rigidly connected to the shaft requires that the screw be positioned in a precisely defined, predetermined angle in the pedicle in order to obtain the desired alignment of the vertebral bodies. In contrast, head pieces that are movable relative to the shaft allow for greater tolerance during insertion of the screw and for a readjustment of the position of the vertebral bodies before the rod system is locked.

With a rod system known from the prior art, the screw is typically screwed into the pedicle with the head piece already attached to the screw. In this method, however, the polyaxial connection between the head piece and the screw proves a hindrance. In an effort to solve this problem, a polyaxial screwdriver was disclosed in EP 2 208 473 A1. In DE 2012 219 630 A1, a rotatable driving profile located within the screw head can be deflected such that it is aligned at all times with the longitudinal axis of the head piece.

In the case of osteoporotic vertebral bodies, securely fixing the screw into the bone in such a way as to prevent the screws from breaking out presents a challenge. In addition, throughout the course of the surgery it is important to minimize the amount of pressure applied to the vertebral bodies. To solve this problem, DE 102 46 177 A1 discloses inserting a cannulated screw, and then injecting filler material into the screw; the filler material exits through windows arranged in the shaft of the screw and fuses with the bone. The head piece is then fixed onto the screw via a head that can be frictionally joined to the shaft.

To enable a quick and uncomplicated surgical procedure, it is desirable for an instrument set of the aforementioned type to comprise a minimal number of individual parts and for these parts to be easily joined to one another.

As is discussed in Eur. Spine J. 2010 January; 19 (1); 144-146, however, in a significant number of patients (5-8%) the stabilizing system must be removed after surgery either because the implant is faulty or because the patient responds negatively to the implant.

In light of these problems in the prior art, it is the object of invention to further develop an instrument set of the aforementioned type in such a way that the burden on the patient during insertion and removal of the screw and the head piece into and from a vertebral body is reduced; it is a further object to provide a method for inserting a screw and a head piece into a vertebral body, and a use of the instrument set to stabilize the spinal column.

According to the invention, this object is attained in that the head piece has a saddle inside the tulip, the saddle having a receiving region for receiving the screw head in a first end region that faces the first insertion opening, and having a coupling region that can be coupled to the tool in a second end region opposite the receiving region, and the saddle being movable between a released position, which can be reached by inserting the screw head, and a locked position, which can be reached by displacing the screw head out of the released position opposite the insertion direction, wherein in the locked position, the screw head that has been received in the receiving region cannot be released from the receiving region, and the tool, which is coupled to the coupling region, can be used to fix the saddle in a released position that enables the release of the screw head from the receiving region.

An instrument set according to the invention comprises the screw, the head piece and the tool, and thus a small number of individual parts. This facilitates a quick surgical procedure. The screw has a shaft, which expediently has a thread for screwing into a pedicle in a screwing-in direction. At the end opposite the screwing-in direction, the screw has a screw head, which can be connected to the head piece. The screw is screwed into the bone without the head piece, and the head piece is then attached to the screw that is fixed in the bone. The screwing-in of the screw thus is not hindered by the head piece.

The head piece has a sleeve-shaped tulip, inside which a saddle is located. The screw head can be inserted in an insertion direction through a first insertion opening in the tulip, into the interior of the tulip.

The saddle has a receiving region for receiving the screw head in a first end region that faces the insertion direction. The head piece can be coupled to the screw via the saddle. According to the invention, the screw head and the saddle are connected in such a way that the shaft of the screw can pivot in relation to the longitudinal axis of the head piece and the head piece can rotate around its longitudinal axis in any pivot position of the shaft. The unit comprising screw and head piece thus forms a polyaxial screw.

In a second end region opposite the receiving region, the saddle has a coupling region which enables it to be coupled to the tool. The tool can be advanced to the coupling region through a second insertion opening in the tulip, opposite the first insertion opening, and can be coupled to said coupling region.

The saddle is able to move in the tulip in the axial direction between a locked position and a released position. In the locked position, the screw head is permanently joined to the receiving region and the head piece is thereby fixedly coupled to the screw. In the released position, the screw head can be connected to the receiving region and disengaged therefrom.

To connect the screw to the receiving region, the saddle must be in the released position. This can be accomplished, for example, by inserting the screw head in the insertion direction through the first insertion opening and into the head piece. The screw head can then abut against the edge of the receiving opening, and the saddle can be pushed from its initial position into the released position by the movement of the screw in the direction of insertion. However, the screw head may also be moved into the released position by means of the tool, as will be described in further detail below. The saddle can then be fixed in the released position by means of the tool, which is coupled to the coupling region. The screw head can then be placed in the receiving region and coupled to the receiving region.

When the head piece and the screw are then moved apart, the saddle coupled to the screw head can be moved into the locked position.

To disengage the screw head from the receiving region, the saddle must be moved into the released position. This can be accomplished with the help of the tool, as will be described in greater detail below. The saddle can then be fixed in the released position by means of the tool, which is coupled to the coupling region. When the screw and the head piece are then moved apart, the tool continues to fix the saddle in the released position, and the screw head can be disengaged from the receiving region.

The connection of the invention between the screw and the head piece is capable of withstanding strong forces, which is absolutely essential in a polyaxial screw for stabilizing the spinal column.

The coupling and separation of the head piece and the screw that is fixed in the pedicle can be accomplished with the help of the tool in such a way that only minimal force is exerted on the vertebral bodies. This is advantageous particularly with osteoporotic bones.

An instrument set according to the invention enables a quick and simple disengagement of the head piece from the screw. And unlike many conventional systems, the screw can be left in the bone. This simplifies the replacement or removal of the head piece considerably and may also result in a shortening of the time required for the surgery.

A further advantageous embodiment of the invention is characterized in that the receiving region, which is delimited by a wall and has a receiving opening for insertion of the screw head, is reversibly deformable in a transverse direction that extends transversely to a longitudinal axis of the tulip. The wall of the receiving region and the receiving opening can then be expanded in the direction of the tulip wall and returned to their original shape. The reversible deformability of the receiving region allows its size to be adjusted, thereby enabling the screw head to be received in and disengaged from the receiving region. The wall and/or the receiving opening may be reversibly deformable.

The receiving region may be elastically deformable. In that case, the screw head can engage in the receiving region. However, the receiving region may also be plastically deformable.

The wall of the receiving region may be configured such that the receiving region is complementary to at least one region of the screw head. At least one portion of the wall of the receiving region and/or the receiving region opening may contact at least one region of the screw head which is arranged in the receiving region. This enables a movement of the screw to result in a movement of the saddle.

Also advantageous is an embodiment in which the wall of the receiving region is subdivided by at least two slots and/or windows into at least two separate sections. The slots and/or windows can enable deformability even if a hard material is chosen for the wall of the saddle. The same material can then be used for the saddle and the tulip. In that case it is advantageous for the slots/windows to breach the edge of the receiving opening with a component perpendicular to the receiving opening. This promotes the deformability or expandability of the receiving opening in a direction transversely to the direction of insertion. The wall may be subdivided by the slots/windows into two or more sections. As the number of separate sections increases, the deformability of the receiving region can be increased. This may, however, also decrease the stability of the connection between the screw head and the receiving region. An embodiment in which the wall is subdivided into four sections is advantageous.

In an advantageous embodiment of the invention, the slots and/or windows may be embodied as T-shaped. In this case it is advantageous for the vertical bar of the T to extend from the receiving opening of the receiving region substantially perpendicular to the receiving opening and to then merge with the horizontal bar of the T, which then extends substantially parallel to the receiving opening or in the circumferential direction of the saddle. With this configuration, the wall has a wall section, spaced at a distance from the receiving opening, the expansion of which parallel to the receiving opening is reduced to a thin material bridge by the horizontal bars of two adjacent T's. If the width of the material bridge is reduced, the deformability of the receiving region is increased or the (restoring) force that counteracts a deformation is decreased.

In a further possible embodiment of the instrument set, at least in the locked position, a wall of the tulip may limit the deformation of the receiving region in the transverse direction. This allows the screw head, in the locked position, to be inseparably connected to the receiving region. If the receiving region is plastically deformable, the wall, which limits the deformation of the receiving region in the locked position, can return the receiving region, which is expanded in the released position, to its original shape in the locked position. In the released position, the wall of the tulip may also limit the deformation of the receiving region in the transverse direction. However, it may also allow unhindered deformation of the receiving region in the released position.

In a further advantageous embodiment of the invention, a first head section of the screw head can have a maximum width BK in a direction perpendicular to the shaft, and a second head section located between the first head section and the shaft can have a second width bK in the direction perpendicular to the shaft, the second width being smaller than the maximum width BK. The screw head may be embodied as spherical, for example. However, it may also be embodied as polyhedral. Preferably, the screw head is in the form of a spherical shell. In that case, the receiving region is preferably complementary to a region of the spherical shell which extends at least from an end region of the screw head opposite the shaft up to the second head section. This allows the screw head to be rotated particularly uniformly in the receiving region. The second width bK may be smaller than the maximum width of the shaft. However, it may also be greater than the maximum width of the shaft.

In a practical embodiment of the invention, when the saddle is in the locked position, the wall of the tulip can limit the maximum expansion of the receiving opening that can be achieved by transverse deformation to a locked expansion (DS), which is smaller than the maximum width (BK) and greater than or equal to the second width (bK) of the screw head, and when the saddle is in the released position, the wall of the tulip can allow a maximum expansion of the receiving opening that can be achieved by transverse deformation to a released expansion (DF), which is equivalent to at least the maximum width (BK) of the screw head. When the saddle is in the locked position and the screw head has been inserted through the first insertion opening into the tulip, a section of the screw head that may coincide with the first head section abuts against the receiving opening in the receiving region. Since the maximum expansion of the receiving opening in the locked position is smaller than the maximum width (BK) of the first head section, when the screw is advanced further in the direction of insertion, the saddle is shifted in the direction of the released position. In that position, the wall of the tulip allows an expansion of the receiving opening to an expansion (DF), which is equivalent to at least the maximum width (BK) of the screw head. When the saddle is then fixed in the released position, for example by means of the tool, and the screw is moved further in the direction of insertion, the screw head exerts pressure on the receiving opening. In the released position, the receiving opening along with the wall of the receiving region can deform in the direction of the wall of the tulip, thereby expanding the receiving region. The receiving opening can expand to a released expansion (DF), which is equivalent to at least the maximum width (BK) of the screw head. This allows the screw head to be inserted into the receiving region. If the wall and the receiving opening of the receiving region are elastically reversibly deformable, then the receiving opening of the receiving region can be decreased again to its original size once the screw head has been inserted. The screw head is then positioned in the receiving region of the saddle, at least partially encompassed by the wall of the receiving region. One section of the screw head may contact the edge of the receiving opening. If the second width (bK) is equal to the expansion of the receiving opening, the second section of the screw head may touch the edge of the receiving opening. When the fixation of the saddle in the released position by means of the tool, which may be necessary, is then released and the screw is moved opposite the direction of insertion, a region of the screw head may come in contact with the receiving opening and the axial force may be transmitted to the saddle, moving the saddle from the released position into the locked position. In the locked position, the maximum expansion of the receiving opening is limited to the locked expansion (DS), which is smaller than the width (BK) of the first head section. As a result, the screw head cannot be disengaged from the receiving region by a movement of the screw and the head piece in the opposite direction.

In a further embodiment of the invention, an inner diameter (DImin) of the tulip at the first insertion opening may be minimal and an inner diameter (DImax) of the tulip in a plane defined by the receiving opening of the saddle in the released position may be maximal. In that case, the wall that delimits the inner region of the tulip can have a recess that encircles the wall in a closed contour in the region of the released position. The wall may, however, also have a plurality of recesses in the region of the released position that are separate from one another and allow an expansion of the receiving opening. The wall that delimits the inner region of the tulip may taper conically from the recess(es) to the first insertion opening.

Also advantageous is an embodiment in which the axial movement of the saddle in the tulip is limited between a first position and a second position. This prevents the saddle from falling out of the tulip. The first and second positions may be selected such that the saddle can move only entirely within the tulip.

According to the invention, the first position may coincide with the released position. The screw head can then be connected to the receiving region without the saddle having to be fixed in the released position by means of the tool. This is because in this embodiment, the screw head inserted into the first insertion opening of the tulip can push the saddle up to the released position. Since the saddle can be moved in the direction of insertion only up to the released position, the saddle is fixed in the released position by the movement of the screw in the direction of insertion, and the pressure exerted by the screw head on the receiving opening causes the receiving opening to expand, allowing the screw head to be inserted into the receiving region.

Also advantageous is an embodiment in which the saddle has at least one projection between the receiving region and the coupling region, which projects up to the wall and engages into a recess formed in the wall of the tulip, wherein the projection, which abuts against first and second stop regions that delimit the recess in the axial direction when the saddle is moved axially, can limit the movement of the saddle between the first and second positions. In this case, the wall may have a single projection. However it may also have a plurality of projections. Preferably, the wall has two projections diametrically opposite one another. The projection may be cuboid in shape. For each projection, a recess is provided in the wall. The recess is embodied such that each projection can engage in its respective recess. Each recess has a first and a second stop region, each region having a component perpendicular to the insertion opening and limiting the expansion of the recess in the axial direction. When the saddle is moved in the direction of insertion, a first stop surface of the projection having a component perpendicular to the direction of insertion abuts against the first stop region, thereby limiting the movement of the saddle in the direction of insertion. This defines the first position. When the saddle is moved opposite the direction of insertion, a second stop surface of the projection having a component perpendicular to the direction of insertion abuts against the second stop region, thereby limiting the movement of the saddle opposite the direction of insertion. This defines the second position. The first and second stop surfaces of the projection are preferably complementary to the surfaces of the first and second stop regions, respectively. As a result, the contact surface of the stop surface that abuts against a stop region is maximal.

The positioning of the projection and the recess may also be interchanged. For instance, the wall may have one or more projections, each of which can engage in a complementary recess in the saddle, thereby limiting the movement of the saddle in the tulip.

In an advantageous embodiment of the invention, the tulip and the saddle may be detachably connected to one another. In that case, the tulip and the saddle can be produced on different production lines and connected to one another either by the manufacturer or by the consumer.

In a further embodiment of the invention, the tulip can have a second insertion opening in a second end region opposite the first insertion opening, said second insertion opening having an edge region in which at least one, preferably two diametrically opposite indentations for receiving a rod of the rod system are formed. The rod can then be inserted into the indentation(s) starting from the second insertion opening. The edge of each indentation may be embodied as U-shaped. In that case, the arms of the U can extend from the insertion opening substantially parallel with the longitudinal axis of the tulip in the direction of the first insertion opening, and can then be connected to one another by the curved portion of the U.

In an instrument set according to the invention, the saddle can have a recess for receiving the rod located in the indentations of the edge region of the tulip, with said recess extending diametrically through the saddle in a second end region located in the direction of the second insertion opening of the tulip. The recess may be embodied as U-shaped. In that case, the arms of the U can extend from the second end region of the saddle substantially parallel to the direction of insertion up to the receiving region, and can then merge into the curved portion of the U before reaching the receiving region. In that case, the curvature of the curved portion of the U and the spacing between the arms are embodied such that the mobility of a cylindrical rod received in the recess in a direction perpendicular to the axis of the rod and perpendicular to an axis of the head piece is minimal.

According to the invention, the tulip may have a locking device located in the second end region for the purpose of fixing the rod. With the locking device, the rod can be secured to the head pieces of the screws that have been screwed into the pedicle, such that the corresponding vertebrae can be fixed in the desired position. The locking device may have an internal thread located in the second end region of the tulip. The internal thread may be screwable to a set screw. This can enable the desired locking of the rod in the head piece.

According to the invention, the tool may comprise a holding grip having a hollow interior and having a coupling member for coupling to the coupling region of the saddle, in which case the coupling member may be at least partially located within the interior space and rotatable about a longitudinal axis (A). The coupling member may be embodied as cylindrical. In addition, the coupling member may have a twist grip in a second end region opposite the first end region. The tool can then be held and guided using the holding grip. The holding grip may have grooves and/or windows that are designed to improve the grip on the holding grip. The coupling member can be rotated around its longitudinal axis using the twist grip. The twist grip may have grooves and/or edges that improve the grip on the twist grip.

In a further embodiment of the invention, the saddle can be non-rotatably arranged in the tulip. According to the invention, the coupling region of the saddle may have an internal thread. Additionally according to the invention, the coupling member of the tool may have an external thread in a first end region, designed to be screwed together with the internal thread of the coupling region. The tool may further have a locking device with which the holding grip can be connected in a rotationally fixed manner to the tulip. The locking device may have two projections that project outward from the holding grip and can be brought into engagement with the recesses of the tulip. The projections may be arranged diametrically opposite one another. In addition, each projection can have a U-shaped contour. In that case, the arms of the U expediently extend from the first edge region of the tool substantially parallel with the longitudinal axis of the tool, and are then connected to one another via the curved portion of the U. This embodiment is particularly advantageous if the end region of the tulip located at the second insertion opening has two U-shaped indentations arranged opposite one another. The U-shaped projections are then expediently embodied as complementary to the U-shaped recesses.

When the external thread of the coupling member of the tool is then screwed to the internal thread of the coupling region of the saddle, since the saddle is arranged rotationally fixed in the tulip and since the holding grip of the tool is coupled to the tulip in a rotationally fixed manner, the rotational movement of the coupling member is converted to an axial movement of the saddle. The saddle can thus be moved from the locked position to the released position. The saddle can also be fixed in the released position by its coupling to the coupling member of the tool.

In a further embodiment of the invention, the coupling member may be displaceable in relation to the holding grip in the axial direction between a first end position and a second end position. In the first end position, the coupling member is retracted into the interior of the holding grip. In this case, the coupling member can be retracted into the interior of the tool far enough that the first end region with the external thread is positioned entirely within the interior space. In the second end position, the coupling member can protrude in the axial direction beyond a first holding grip end region of the holding grip located in the direction of the coupling member. The coupling member can be displaced, for example, by holding the tool by the holding grip and holding the coupling member by the twist grip and then moving the coupling member in the axial direction. This allows the screwing of the coupling member into the coupling region to be simplified as follows: The tool can be connected in a rotationally fixed manner to the tulip using the coupling member located in the first end position via the locking device of the tool. When the first end region of the coupling member is located entirely within the interior space of the tool, the tool can be connected particularly easily to the tulip. The coupling member can then be pushed toward the second end position and thus toward the tulip until the external thread of the coupling member can be brought into engagement with the internal thread of the coupling region of the saddle. By turning the twist grip, the coupling member can then be screwed into the coupling region. As described above, the rotational movement of the coupling member can be converted into an axial movement of the saddle, and the saddle can be moved into the released position.

In an instrument set according to the invention, the screw may be solid or cannulated and/or fenestrated. A cannulated screw can be screwed into the bone with the help of a guide wire. The guide wire can facilitate positioning of the screw. In the case of a cannulated and fenestrated screw, a fill material may also be injected into the cannula, exiting through the windows and fusing with the bone. This can facilitate fixation in osteoporotic bone.

In an instrument set according to the present invention, screws having a screw length of 30 mm to 100 mm are preferably used. Screws having a shaft diameter of 4.5 mm or 5.5 mm or 6.5 mm or 7.5 mm or 8.5 mm or 9.5 mm are preferably used.

According to the invention, the screw may have a first thread with a first thread pitch and a second thread with a second thread pitch, and the first and second thread pitches may be the same or different. The use of different thread pitches can allow traction or pressure to be exerted on a bone or can even allow splintered bone pieces to be joined together.

The screw may also be embodied such that the first thread pitch and the second thread pitch are the same and the two threads are arranged along the shaft of the screw in such a way that the screw is double-threaded in a second shaft region adjacent to the screw head and is single-threaded in a first shaft region extending away from the second shaft region opposite the screw head. The anchoring of the screw in the bone can thereby be improved.

In a further embodiment of the invention, the screw head can have a recess for receiving a screwdriver. The recess may be embodied as a square socket, a hexagonal socket (Allen), a hexalobular socket (Torx) or a serrated socket (XZN).

In this description, the head piece is described in conjunction with the screw and the tool. However, protection is also being sought for the head piece alone, without the screw and the tool.

In this description, the head piece and the screw are described in conjunction with the tool. However, protection is also being sought for the head piece and the screw, without the tool.

In this description, the tool is described in conjunction with the head piece and the screw. However, protection is also being sought for the tool alone, without the head piece and the screw.

The invention further provides a method for inserting and for removing a screw according to the invention and a head piece according to the invention into and from a vertebral body, for example as part of a spinal surgery. In this method, first a guide wire can be emplaced. The guide wire can facilitate the setting of a cannulated screw in the correct position in the vertebral body. The screw may, however, also be screwed into the vertebral body without the guide wire. A screwdriver can be coupled to the recess of the screw head and the screw can be screwed into the pedicle. If a cannulated and fenestrated screw is used, the fixation of the screw in the bone can be improved by injecting a suitable material into the cannula of the screw, which then exits through the windows of the screw and fuses with the bone, particularly with an osteoporotic bone. The tool can then be coupled in a rotationally fixed manner to the tulip by means of the locking device. Locking may be accomplished, for example, by bringing two projections that are arranged diametrically opposite one another in the first holding grip region into engagement with two U-shaped indentations that are arranged diametrically opposite one another and formed in the edge region of the second insertion opening. The coupling member can thereby be held in the first position. The tool can be held by its holding grip. The coupling member can be pushed through the second insertion opening in the tulip toward the second end position, until the coupling member abuts against the coupling region of the saddle. The twist grip of the coupling member can then be rotated, allowing the external thread of the coupling member to be screwed into the internal thread of the saddle. The rotational movement of the coupling member can thereby be converted into an axial movement of the saddle, as described above. The saddle can thus be moved into the released position. The saddle can be fixed in the released position by means of the tool. The head piece can then be moved with the first insertion opening up to the screw head of the screw that has been screwed into the pedicle. With this movement, the screw head can be guided in the direction of the saddle. Since the saddle is fixed in the released position, the screw head can be inserted without pressure into the receiving region.

The coupling member can then be unscrewed from the internal thread of the saddle by rotating the twist grip. This allows the saddle to be moved into the locked position. This method of insertion exerts only a small amount of pressure on the vertebrae and is particularly advantageous in the case of osteoporotic bone. The tulip is then connected polyaxially to the screw. The head piece may, however, also be mounted on the screw head without the tool. To accomplish this, the head piece can be introduced into the screw in such a way that the screw head enters into the first insertion opening in the tulip. The head piece can be advanced further toward the screw. This allows the head of the screw to abut against the receiving opening of the saddle. The saddle can thereby be shifted from the locked position into the released position. If the released position coincides with the first position, the saddle cannot be moved any further in the direction of insertion. If the head piece is moved further toward the screw, the screw head will exert pressure on the receiving opening. This may cause the receiving region to expand in the radial direction. The screw head is then able to pass through the widened receiving opening into the receiving region. If the deformation of the receiving region is elastic, the receiving opening can then return to its original size. The screw head is snapped into the receiving region, and the screw is securely joined to the head piece.

In contrast to conventional methods, the method according to the invention for inserting the screw according to the invention and the screw head according to the invention does not entail the problem of a head piece which is polyaxially connected to the screw hindering the screwing of the screw into the pedicle.

The head piece can be easily disengaged from the screw by means of the tool. To accomplish this, the tool can be held by the holding grip and the coupling member can be moved to the first end position. In the first end position, the first end region of the coupling member having the external thread may be located entirely within the interior space of the holding grip. The tool can then be coupled with the locking device to the tulip in a rotationally fixed manner. Locking can be accomplished, for example, by bringing two projections that are arranged diametrically opposite one another in the first holding grip region into engagement with two U-shaped indentations that are arranged diametrically opposite one another and are formed in the edge region of the second insertion opening. The first end region of the coupling member having the external thread can then be pushed through the second insertion opening into the head piece and up to the coupling region of the saddle. The coupling member can then be rotated by means of the twist grip, thereby screwing the coupling member into the coupling region of the saddle. This rotational movement allows the saddle to be moved axially into the released position. The head piece can then be disengaged from the screw head with little applied force by moving the tool with the saddle coupled thereto away from the screw.

This method allows the head piece to be detached from the screw easily, quickly and with little force applied. This enables the head piece to be removed from the body easily without removing the screw from the bone.

An instrument set according to the invention can be used for stabilizing the spinal column. In such a process, first screws according to the invention can be screwed according to the method described above into each of the two pedicles of the vertebral bodies to be connected. A head piece according to the invention can then be attached to each of the screws, as described above. The head pieces can be attached with or without the help of the tool. One rod can then be joined to each of the head pieces arranged lengthwise along the spinal column. Since the head pieces are connected polyaxially to the screws, the rods can be inserted more easily than if the head pieces were rigidly connected to the screws. The polyaxial connection between the head piece and the screw then allows the positioning of the vertebral bodies to be readjusted. Finally, the two rods can be locked in the predetermined position by means of the locking device. The vertebral bodies are then fixed in a predetermined position.

The screw, the tulip and the saddle may be made of the same material, for example Ti-6Al-4V. They may, however, also be made of different materials. The material may include a stainless steel, for example, Co-28Cr-6Mo or X2CrNiMo18-15-3 (1.4441). It may also be made of a different material.

BRIEF DESCRIPTION OF DRAWINGS

In the following description, the invention will be specified in greater detail by way of example, with reference to the set of drawings. In the drawings, FIG. 4 shows the insertion of the saddle shown in FIG. 3 into the tulip shown in FIGS. 1a, 1b and 2, FIG. 5 on the left side is a cross-sectional view and on the right side is a plan view of the head piece of FIGS. 1a and 1b along the line B-B, with a tulip and a saddle according to one embodiment of the invention.

DETAILED DESCRIPTION

Figure 1A:
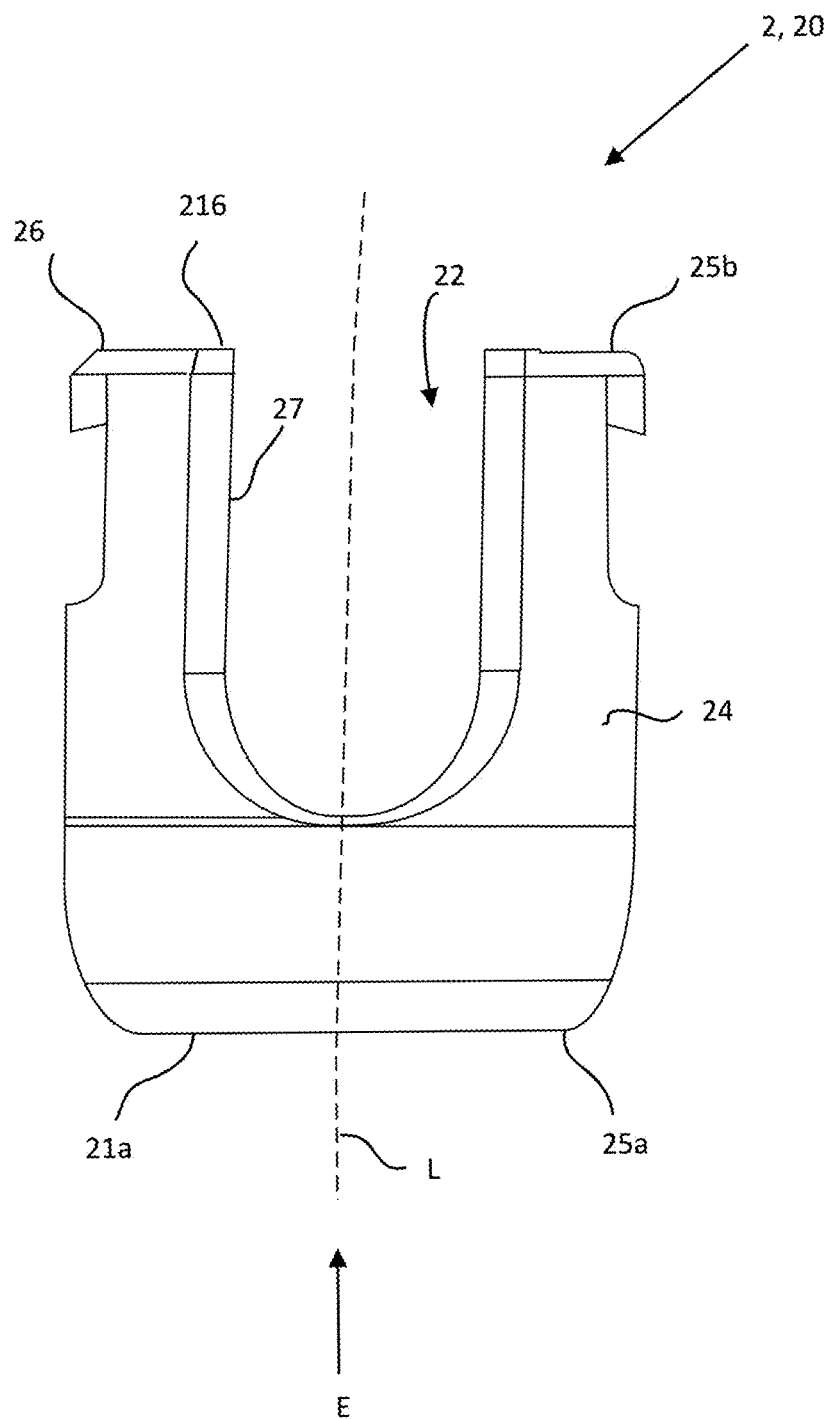
FIG. 1a is a plan view of a head piece/a tulip of an instrument set according to one embodiment of the invention, having two diametrically opposed indentations.
Figure 1B:
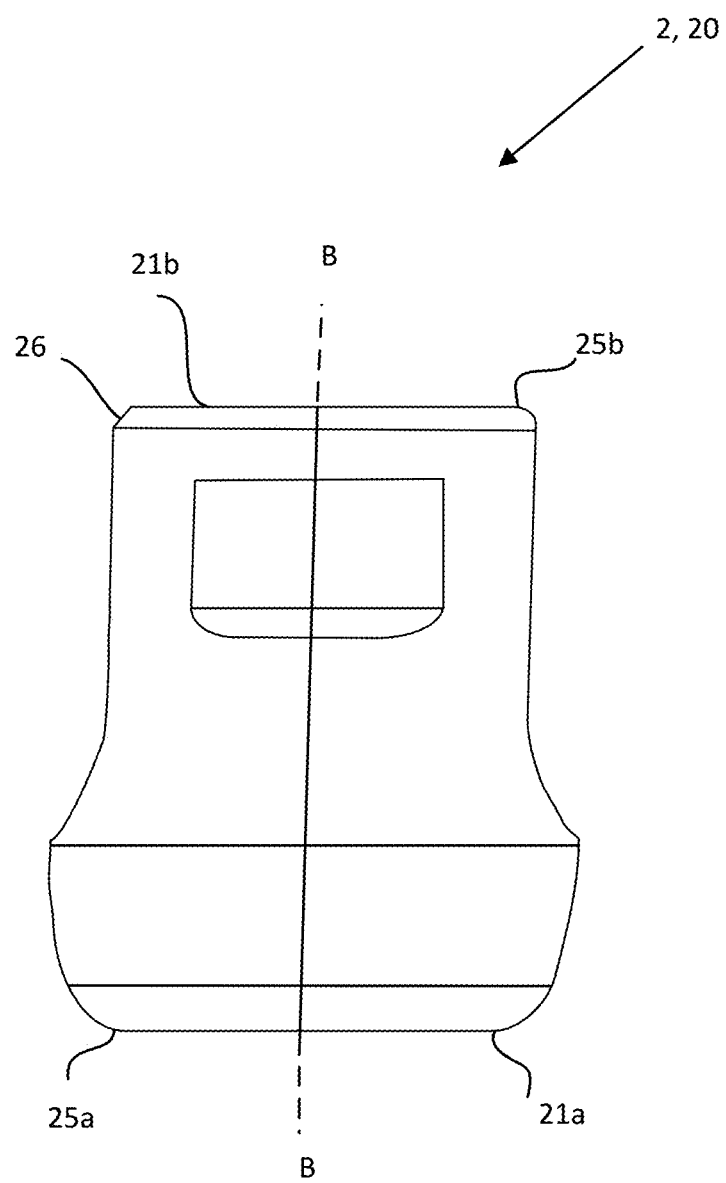
FIG. 1b is a plan view of the head piece/tulip of FIG. 1a rotated 90° around the longitudinal axis L.

FIG. 1a shows a plan view of a head piece 2 of an instrument set 1, the head piece having a tulip 20. Head piece 2 is sleeve-shaped and has a longitudinal axis L. FIG. 1b shows head piece 2 with tulip 20 as shown in FIG. 1a, rotated 90° around longitudinal axis L in relation to FIG. 1a. In a first end region 25a, tulip 20 has a first insertion opening 21a, into which a screw head 12 can be inserted in a direction of insertion E into the interior region 22 of tulip 20. In a section end region 25b opposite first insertion opening 21a, tulip 20 has a second insertion opening 21b for inserting tool 40. Edge region 26 of second insertion opening 21b has two indentations 27. The indentations 27 are located diametrically opposite one another. Indentations 27 are embodied as U-shaped, with the arms of the U extending from second insertion opening 21b substantially parallel to longitudinal axis L through wall 24 of tulip 20 and joining one another via the curved portion of the U. A rod 101 of a rod system 100 may be positioned in indentations 27.

Figure 2:
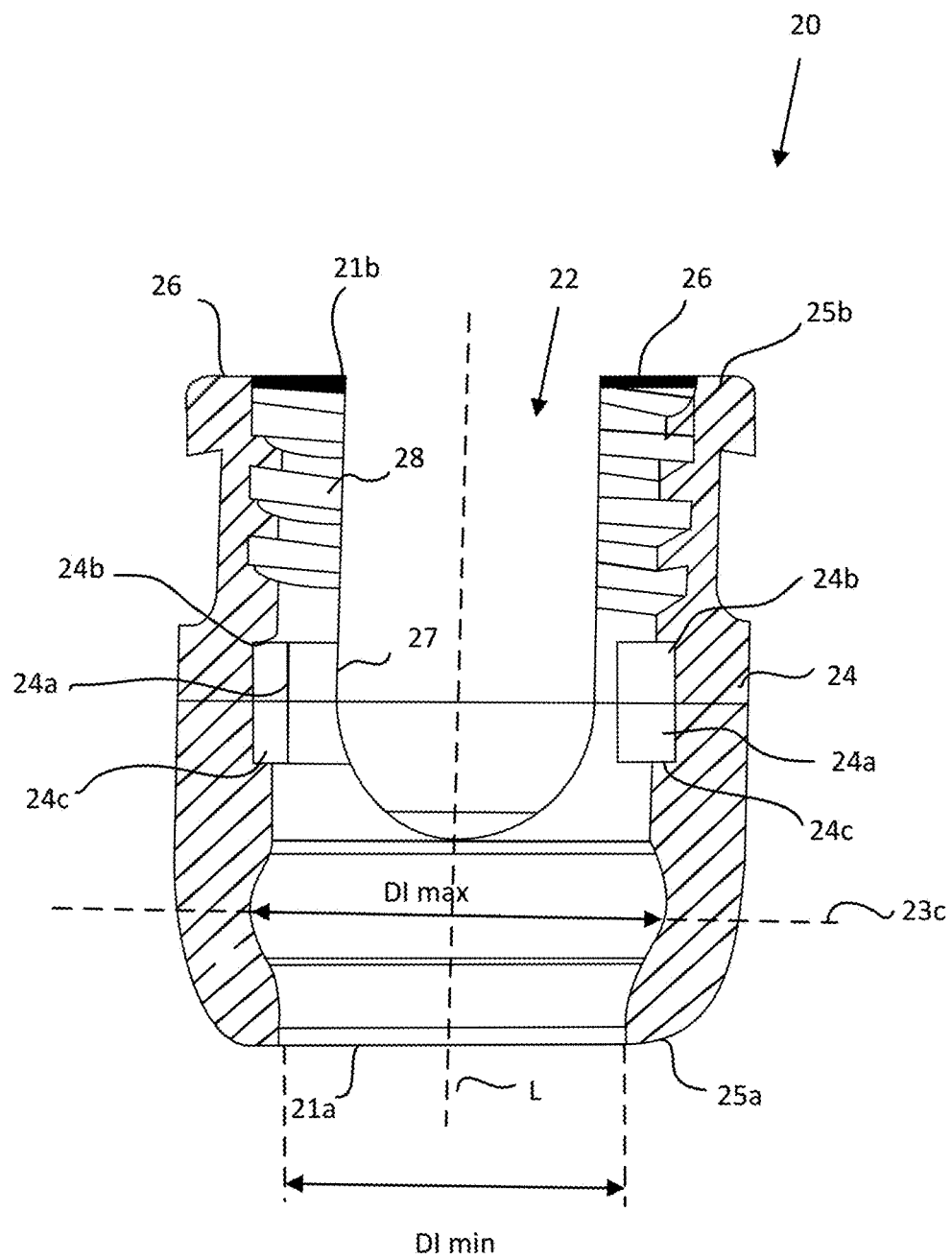
FIG. 2 is a cross-sectional view of the tulip shown in FIGS. 1a and 1b along line B-B (see FIG. 1b)

FIG. 2 shows a cross-section of head piece 2 having a tulip 20 as shown in FIGS. 1a and 1b, along line B-B (see FIG. 1b). An inner diameter DI min of tulip 20 is minimal at first insertion opening 21a. Tulip 20 further has a maximal inner diameter DI max in a plane 23c. In the region of plane 23c, wall 24 of tulip 20 has two recesses 24a, diametrically opposite one another, on its side facing interior region 22 of tulip 20. Each of the recesses 24a is limited in the axial direction by a first stop region 24b and a second stop region 24c. First and second stop regions 24b and c extend substantially perpendicular to longitudinal axis L of tulip 20.

Figure 3:
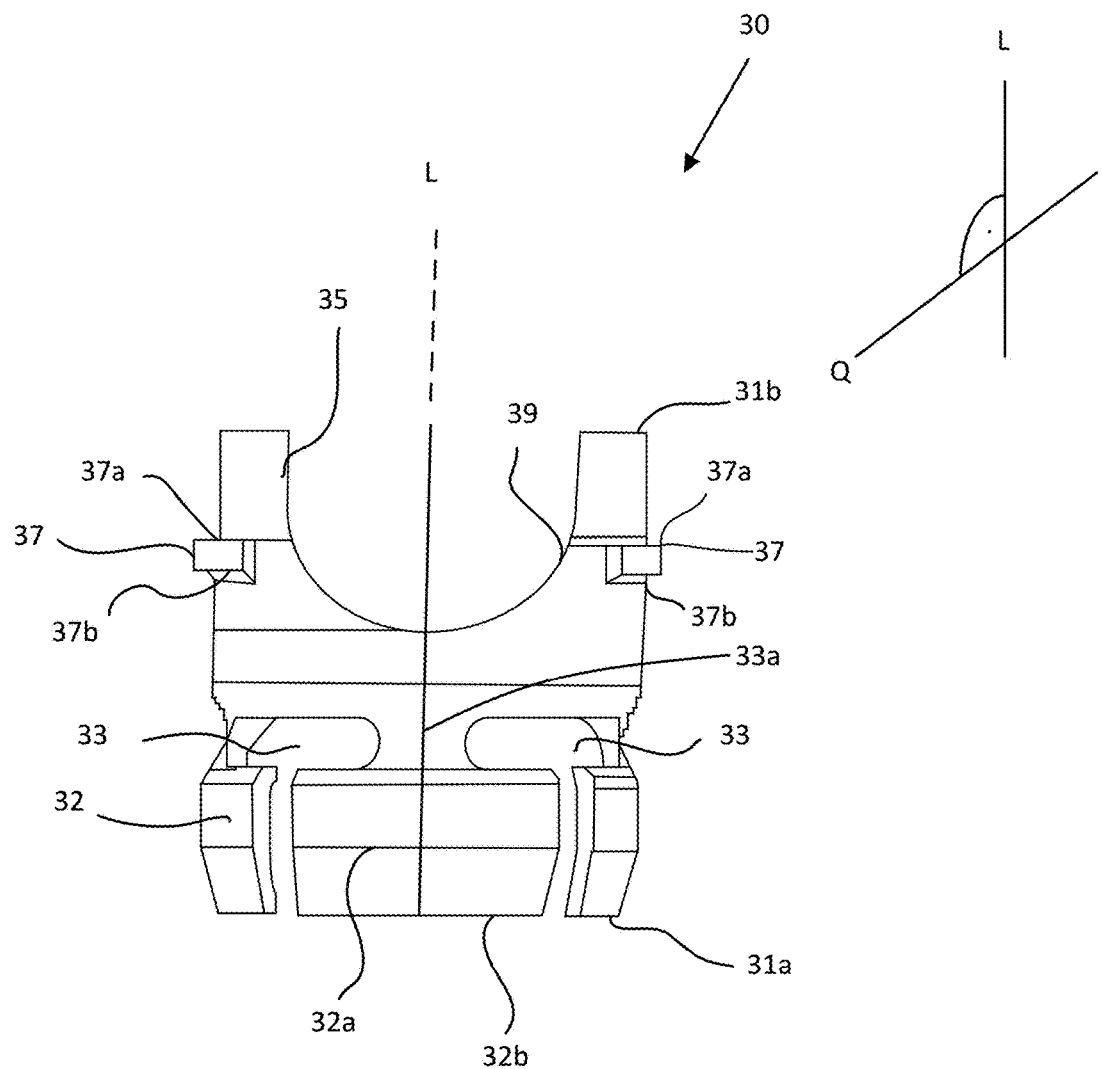
FIG. 3 is a plan view of a saddle of an instrument set according to one embodiment of the invention.

FIG. 3 shows a plan view of a saddle 30 of an instrument set 1 according to one embodiment of the invention. Saddle 30 has a receiving region 32 in a first end region 31a for receiving screw head 12. Receiving region 32 is delimited by a wall 32a and has a receiving opening 32b, through which screw head 12 can be inserted into receiving region 32. Wall 32a of receiving region 32 has a plurality of slots 33. Slots 33 subdivide wall 32a of receiving region 32 into a plurality of regions, separated from one another. Slots 33 are embodied as T-shaped. The vertical bar of the T in each case extends substantially perpendicular to the edge of receiving opening 32b through wall 32a of receiving region 32, and then merges into the horizontal bar of the T. As a result, wall 32a of receiving region 32 comprises only a narrow material bridge 33a between two adjacent T-shaped slots 33, in a region between first end region 31a and a second end region 31b located opposite first end region 31a. This enables a reversible deformation of receiving opening 32b and of receiving region 32 in a transverse direction Q extending perpendicular to a longitudinal axis L of tulip 20. Second end region 31b has a coupling region 35 for coupling to tool 40. Saddle 30 further has, in second end region 31b, a recess 39 extending diametrically through saddle 30. Rod 101, which can be positioned in indentations 27 of edge region 26 of tulip 20, can be received in recess 39. Recess 39 is embodied as U-shaped. The arms of the U extend substantially parallel to the longitudinal axis L' of saddle 30 and are then connected to one another by the curved portion of the U. Between first end region 31a and second end region 31b of saddle 30, saddle 30 has two projections 37, diametrically opposite one another. Projections 37 each have a component perpendicular to longitudinal axis L' of saddle 30. As will be described further below, projections 37 can engage in recesses 24a of tulip 20 and thereby limit the axial movement of saddle 30 in tulip 20 between a first position L1 and a second position L2.

FIGS. 4a to g show the insertion of saddle 30 as shown in FIG. 3 into tulip 20 as shown in FIGS. 1a, 1b and 2. As shown in FIG. 4a, saddle 30, leading with receiving region 32, is inserted through second insertion opening 21b into tulip 20. During insertion, saddle 30 is aligned in relation to tulip 20 such that the two diametrically opposing projections 37 of saddle 30 coincide with the U-shaped indentations 27 of tulip 20.

As shown in FIG. 4b, saddle 30 is inserted into tulip 20 until the projections 37 reach the level of the recesses 24a that are located in wall 24 of tulip 20.

As shown in FIG. 4c, saddle 30 is then rotated in relation to tulip 20 so that projections 37 are introduced into recesses 24a of tulip 20. Saddle 30 can thereby be connected to tulip 20 in a rotationally fixed manner.

FIG. 4d shows saddle 30 positioned rotationally fixed in tulip 20. FIG. 4e shows the plan view of tulip 20 into which saddle 30 has been inserted, as shown in FIG. 1a. Longitudinal axis L of tulip 20 is substantially coincident with longitudinal axis L' of saddle 30. FIG. 4f is an enlarged illustration of the section marked by a circle in FIG. 4b. Here, saddle 30 has not yet been connected rotationally fixed to tulip 20. FIG. 4g shows an enlargement of the section marked by a circle in FIG. 4c. Saddle 30 is rotated in relation to tulip 20 so as to introduce projection 37 into recess 24a of tulip 20, thereby connecting saddle 30 in a rotationally fixed manner to tulip 20.

Figure 5:
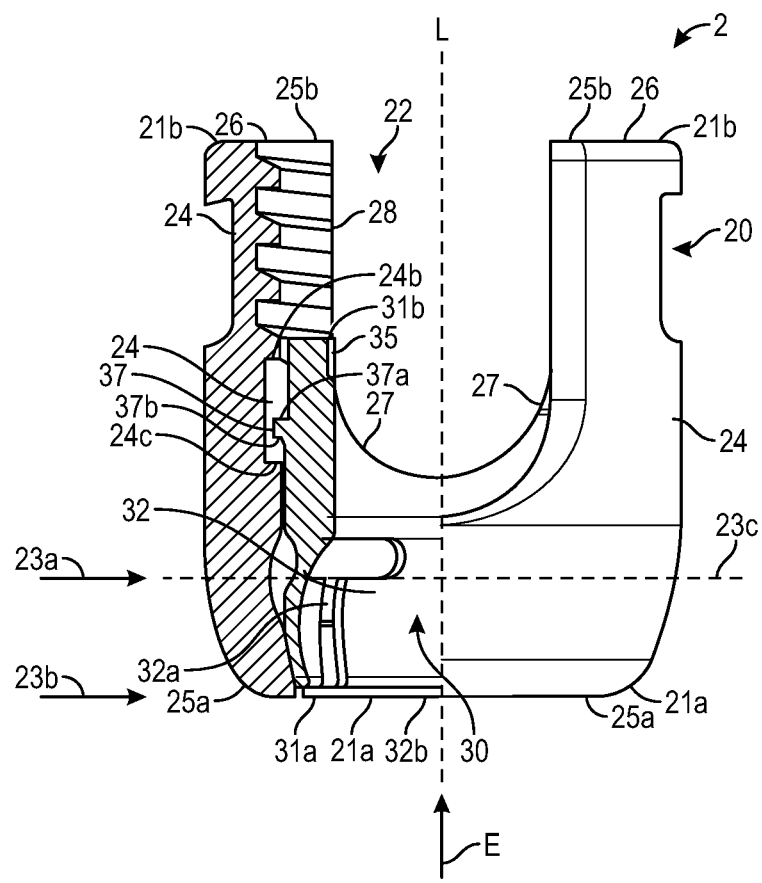

FIG. 5 shows head piece 2 as illustrated in FIG. 1a. The right side of FIG. 5 shows a plan view of head piece 2. The left side of FIG. 5 shows a cross-sectional view of head piece 2 along line B-B (see FIG. 1b). Saddle 30 has been inserted into tulip 20. Receiving opening 32b of saddle 30 and first insertion opening 21a of tulip 20 lie approximately in the same plane. Saddle 30 is situated in the locked position 23b. As is clear from the figure, the maximum diameter of receiving opening 32b is limited by the minimum inner diameter DImin of tulip 20 at first insertion opening 21a to a locked expansion DS. When saddle 30 is moved axially in tulip 20 in direction of insertion E such that receiving opening 32b is disposed in plane 23c, saddle 30 is situated in released position 23a. Receiving opening 32b is then able to expand to released expansion DF, which is greater than the maximum diameter of screw head 12, and therefore screw head 12 can be inserted into receiving region 32 and removed from receiving region 32. Saddle 30 has a projection 37 extending in the direction of wall 24 of tulip 20. Projection 37 has a first stop surface 37a and a second stop surface 37b. First stop surface 37a and second stop surface 37b have a component perpendicular to longitudinal axis L of tulip 20. When saddle 30 is displaced in tulip 20 in direction of insertion E, first stop surface 37a of projection 37 abuts against first stop region 24b of recess 24a. This defines the first position L1 of saddle 30. Saddle 30 cannot be pushed beyond first position L1 in insertion direction E. When saddle 30 is moved opposite insertion direction E, second stop surface 37b of projection 37 abuts against second stop region 24c. This defines second position L2 of saddle 30. Saddle 30 cannot be moved beyond second position L2 opposite insertion direction E. The movement of saddle 30 is therefore limited in the axial direction between first position L1 and second position L2. In particular, saddle 30 is prevented from falling out of tulip 20. Sleeve-shaped tulip 20 has a second insertion opening 21b in a second end region 25b located opposite first insertion opening 21a. Tool 40 can be inserted through second insertion opening 21b into tulip 20. Tool 40 can then be coupled to coupling region 35 of saddle 30. Coupling region 35 may have an internal thread 38 for this purpose. Edge region 26 of second insertion opening 21b has two U-shaped indentations 27 arranged diametrically opposite one another for receiving a rod 101 of a rod system 100. Second end region 31b, which is located opposite receiving region 32 of saddle 30, further has a U-shaped recess 39 extending diametrically through saddle 30 and designed for the receiving rod 101 that is positioned in indentations 27 in tulip 20. Rod 101 can then be fixed in tulip 20 by means of a locking device 28 located in second end region 25b of tulip 20. As shown in FIG. 5, locking device 28 may be embodied as an internal thread. A set screw 50 can be screwed to the internal thread, for example; this fixes rod 101 in head piece 2.

Figure 6A:
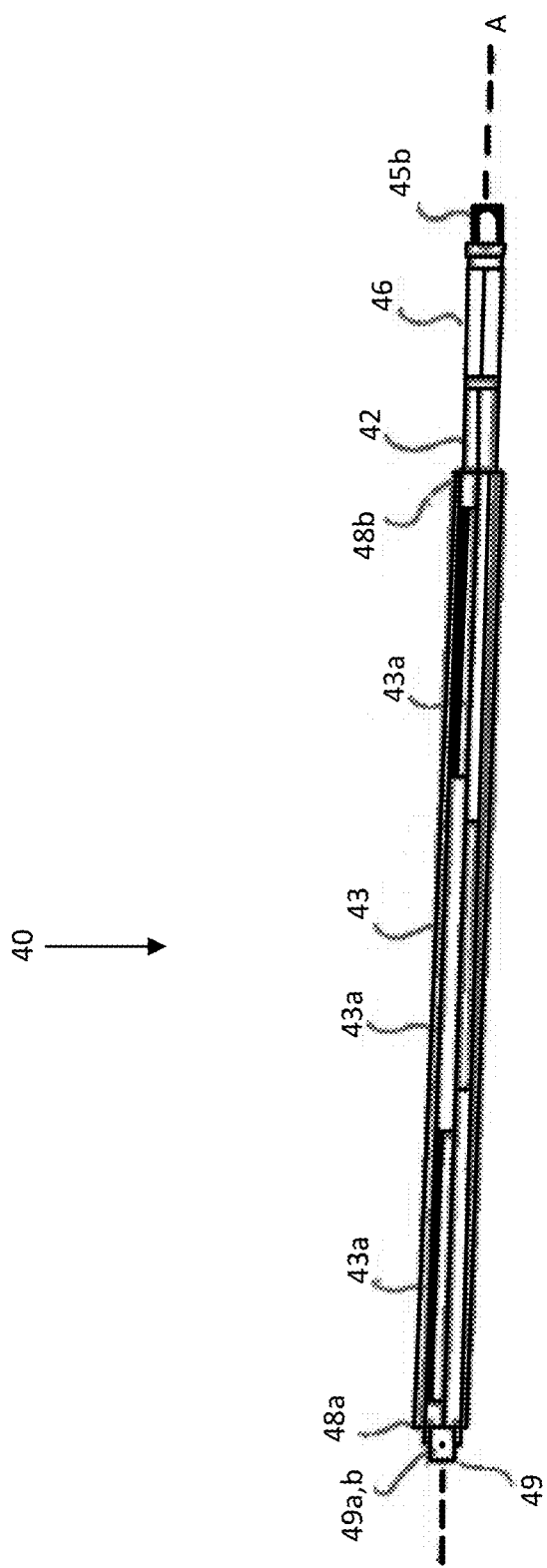
FIG. 6a is a plan view of a tool of an instrument set according to one embodiment of the invention.

FIG. 6a shows a plan view of a tool 40 of an instrument set 1 according to one embodiment of the invention. Tool 40 has an elongated holding grip 43. Interior space 44 of holding grip 43 has a cavity in which a cylindrical coupling member 42 is disposed. Coupling member 42 can be displaced in relation to holding grip 43 axially between a first end position 47a and a second end position 47b. In first end position 47a, coupling member 42 is retracted far enough into interior space 44 of holding grip 43 that the first end region 45a of coupling member 42, which is situated facing first holding grip end region 48a, is located within interior space 44 of holding grip 43. This case is shown in FIG. 6a. In second end position 47b, first end region 45a of coupling member 42 projects beyond first holding grip end region 48a of holding grip 43 (not shown). Coupling member 42 is arranged rotatably about its longitudinal axis A in interior space 44 of holding grip 43. Tool 40 can be held by holding grip 43, and coupling member 42 can be rotated using its twist grip 46 in relation to holding grip 43. Holding grip 43 has a locking device 49 in a first holding grip end region 48a situated opposite twist grip 46 of coupling member 42. Locking device 49 comprises a first projection 49a and a second projection 49b. First projection 49a and second projection 49b can be brought into engagement with the diametrically opposing indentations 27 in edge region 26 of tulip 20, whereby tool 40 can be coupled in a rotationally fixed manner to tulip 20.

Figure 6B:
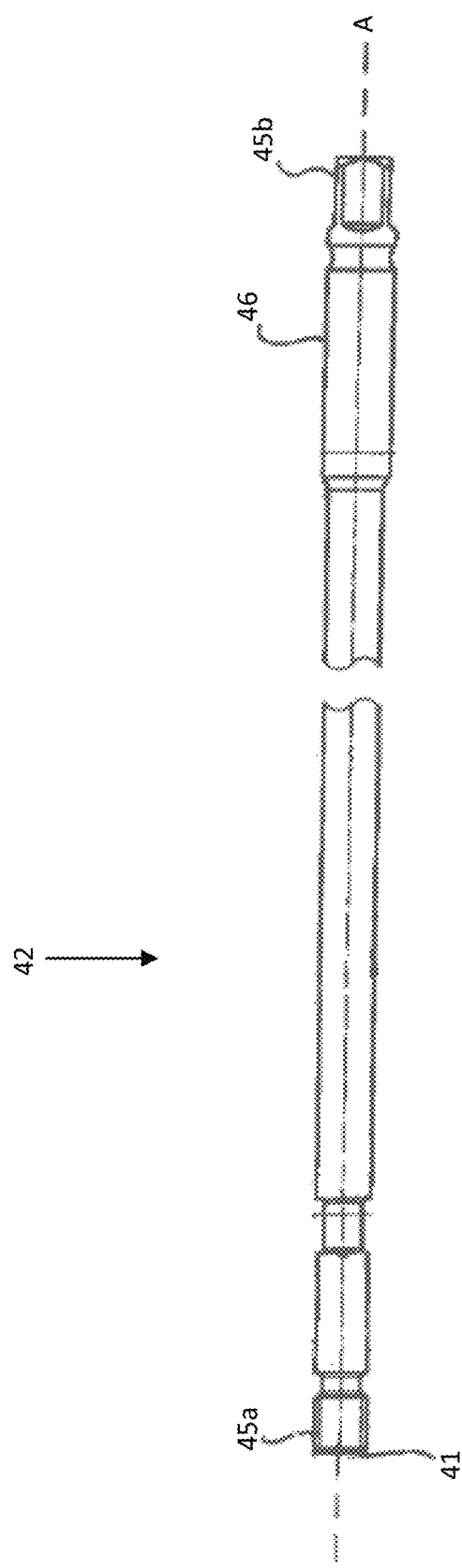
FIG. 6b is a plan view of the coupling member of the tool shown in FIG. 6a, FIG. 6c is a plan view of the holding grip of the tool shown in FIG. 6a, FIG. 7 is a plan view of a screw of an instrument set according to one embodiment of the invention.

FIG. 6b shows a plan view of coupling member 42 of tool 40, shown in FIG. 6a. Coupling member 42 is embodied as cylindrical and has a first end region 45a and a second end region 45b. A twist grip 46 is provided in second end region 45b. First end region 45a of coupling member 42 can be coupled to coupling region 35 of saddle 30. For this purpose, first end region 45a has an external thread 41, which can be screwed to an internal thread 38 situated in coupling region 35 of saddle 30.

Figure 6C:
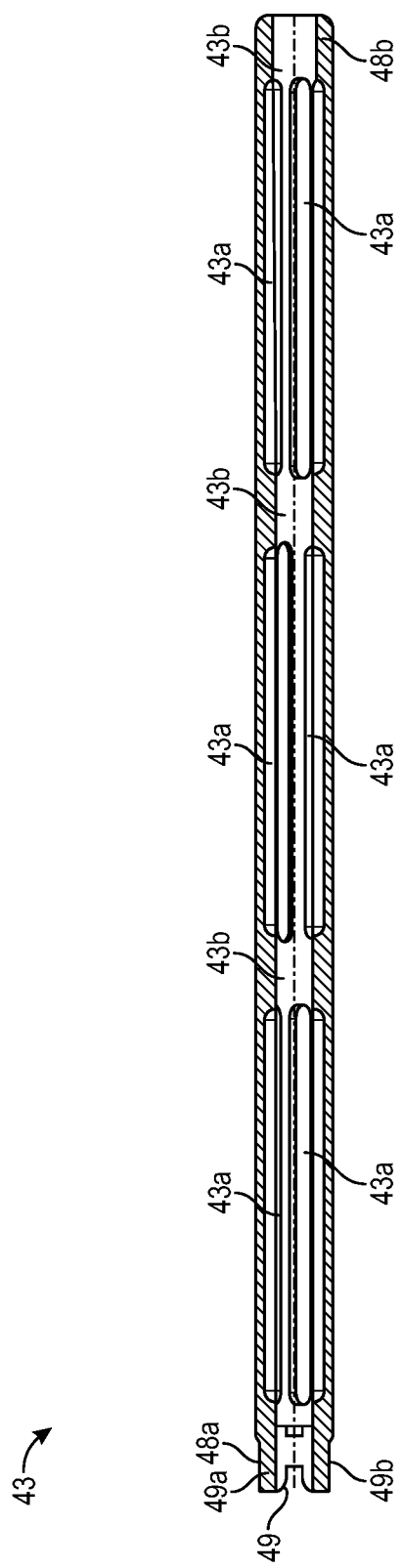

FIG. 6c shows a plan view of holding grip 43 of tool 40 shown in FIG. 6a. Holding grip 43 is embodied as elongated. The wall of holding grip 43 has grooves 43a and windows 43b, which improve the grip of holding grip 43. Tool 40 has a first holding grip end region 48a and a second holding grip end region 48b. First holding grip end region 48a is situated in the direction of first end region 45a of the coupling member 42 inserted into holding grip 43. Second holding grip end region 48b is situated at the end of holding grip 43 that is opposite the first holding grip end region. A locking device 49 is situated in first holding grip end region 48a of tool 40. Locking device 49 can be used to couple tool 40 in a rotationally fixed manner to tulip 20. Locking device 49 comprises a first projection 49a and a second projection 49b. First projection 49a and second projection 49b are situated diametrically opposite one another and are configured such that they can be brought into engagement with the diametrically opposed indentations 27 of edge region 26 of tulip 20.

Figure 7:
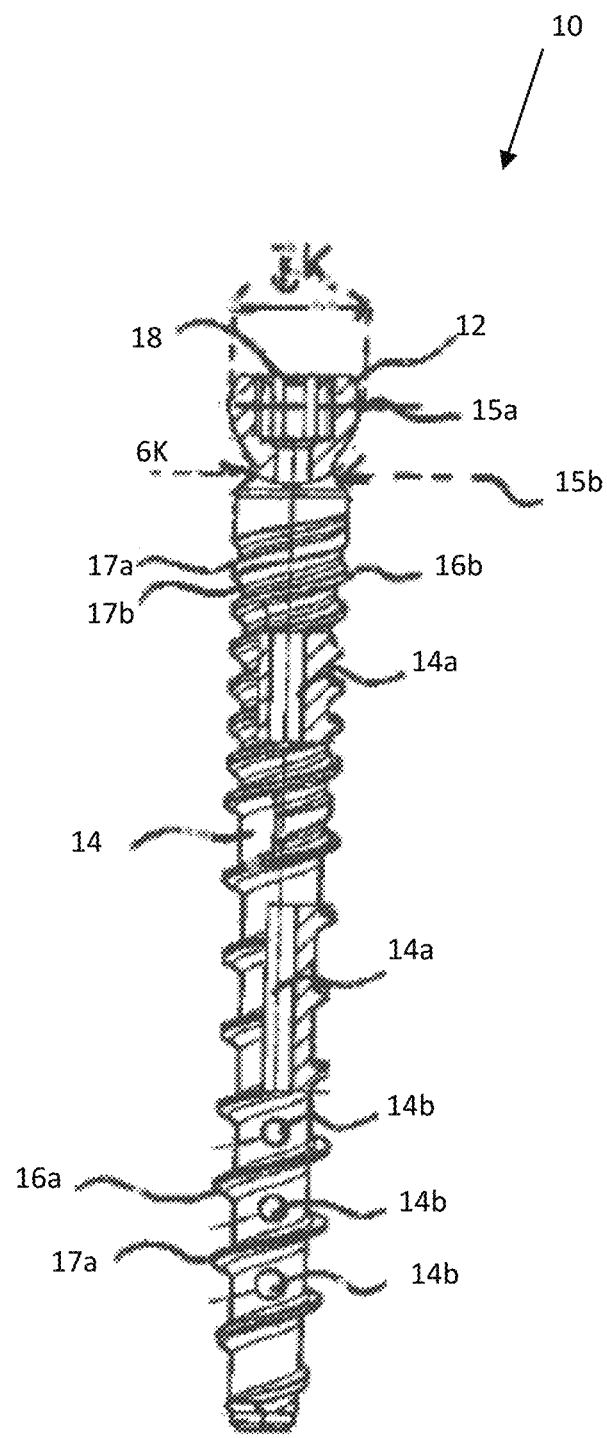

FIG. 7 shows a plan view of a screw 10 of an instrument set according to one embodiment of the invention. Screw 10 has a shaft 14 to be screwed into a bone. A first thread 17a and a second thread 17b are provided on shaft 14. First thread 17a and second thread 17b have the same thread pitch. First thread 17a extends along the entire shaft 14. Second thread 17b extends only along a second shaft region 16b that borders screw head 12. Screw 10 thus has a double thread in second shaft region 16b. In a first shaft region 16a, bordering the second shaft region 16b and extending from this region away from screw head 12, screw 10 has a single thread. As shown in FIG. 7, shaft 14 has a cannula 14a. This enables screw 10 to be guided via a guide wire as it is screwed into a bone. Shaft 14 of screw 10 further has windows 14b. When screw 10 is screwed into an osteoporotic bone, for example, the fixation of screw 10 in the bone can be improved by injecting a material into cannula 14a of screw 10, which then exits through windows 14b and fuses with the bone. Screw head 12 is attached to shaft 14 of screw 10. Screw head 12 is in the form of a spherical disk. Screw head 12 has a first head region 15a, which is characterized in that screw head 12 has a maximum width BK in a direction perpendicular to shaft 14. Situated between first head region 15a and shaft 14 is a second head region 15b, which has a second width bK, which is smaller than maximum width BK, in the direction perpendicular to shaft 14. This configuration of screw head 12 enables screw head 12 to be inseparably connected to receiving region 32 of saddle 30 when saddle 30 is in locked position 23b.

Figure 8:
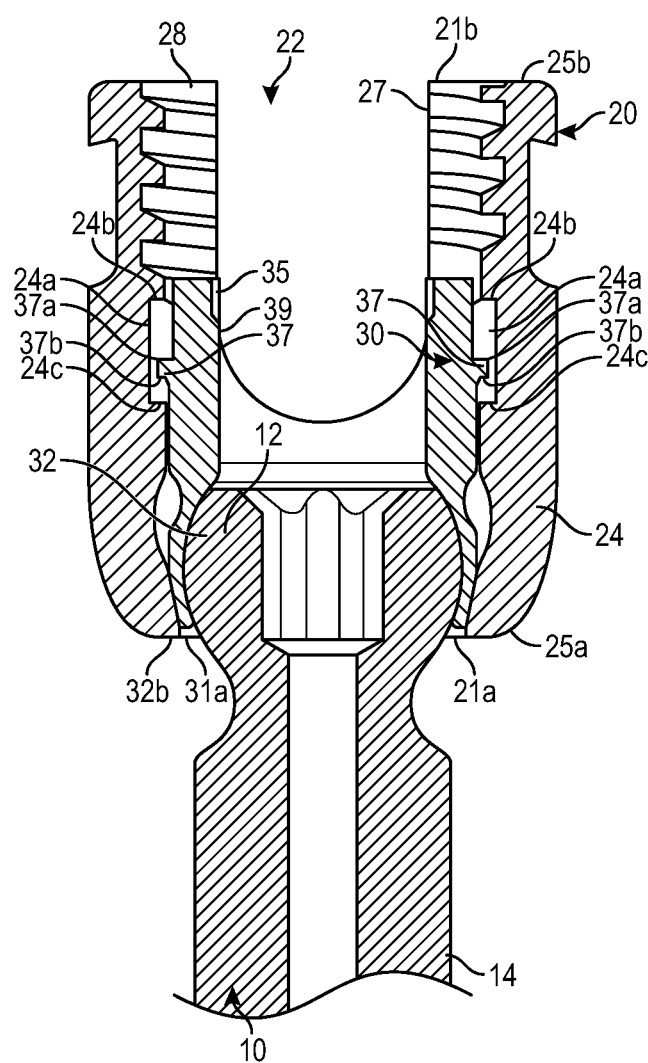
FIG. 8 is a cross-section along the line B-B of the head piece shown in FIGS. 1a and 1b, connected to the screw shown in FIG. 7, FIG. 9 a-d is a cross-sectional view along line B-B of the head piece shown in FIGS. 1a and 1b, being separated by means of the tool shown in FIGS. 6a to 6c from the screw shown in FIG. 7.

FIG. 8 shows a cross-sectional view along line B-B of head piece 2, shown in FIGS. 1a and 1b, which is connected to screw 10, shown in FIG. 7. Screw head 12 is situated in receiving region 32 of saddle 30. Saddle 30 is located in tulip 20 in the locked position 23b. The maximum expansion of receiving opening 32b is limited here to a locked expansion DS. Locked expansion DS is smaller than the maximum width BK of screw head 12. When screw 10 and head piece 2 are moved in opposite directions away from one another, saddle 30 cannot be moved beyond second position L2 due to projection 37, located on saddle 30, which engages into recess 24a which is formed in wall 24 of tulip 20. The maximum expansion of receiving opening 32b is also limited to the locked expansion DS in second position L2. Screw 10 is thus inseparably connected to head piece 2.

Figure 9A:
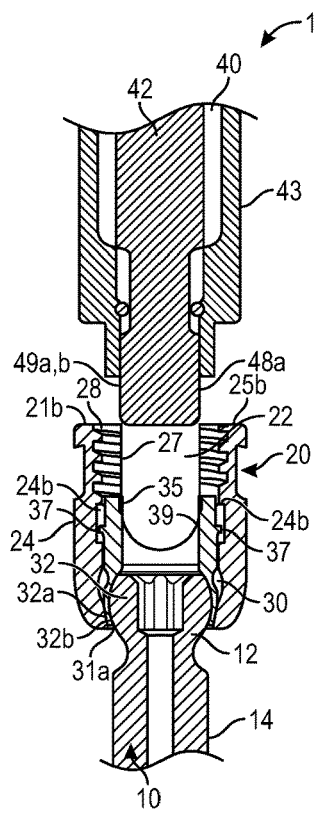

FIGS. 9a to d show a cross-sectional view along line B-B of head piece 2 shown in FIGS. 1a and 1b, which is separated by means of tool 40, shown in FIGS. 6a to 6c, from screw 10, shown in FIG. 7. FIG. 9a shows head piece 2 connected to screw 10. Screw head 12 is situated in receiving region 32 of the saddle. Saddle 30 is in the locked position 23b. First holding grip end region 48a of tool 40 is advanced to second insertion opening 21b of tulip 20, which is located in second end region 25b. In first end position 47a, coupling member 42 is located in interior 44 of holding grip 43 of tool 40.

Figure 9B:
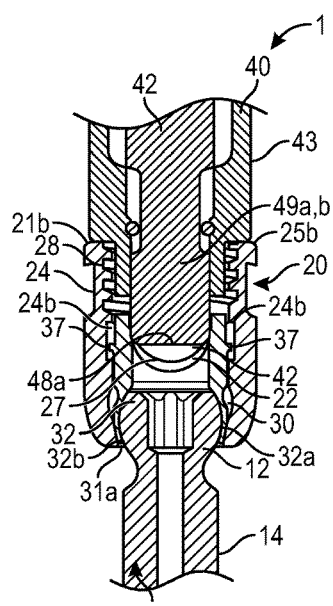

FIG. 9b shows tool 40 now coupled in a rotationally fixed manner to tulip 20. The first and second projections 49a, b located in the first holding grip end region 48a have now been brought into engagement with the two diametrically opposed indentations 27 of edge region 26 of second insertion opening 21b. Saddle 30, connected to screw head 12, is situated in locked position 23b. Coupling member 42 has been moved from first end position 47a opposite the direction of insertion toward second end position 47b, and now protrudes slightly beyond the first holding grip end region 48a. Coupling member 42 has been moved opposite insertion direction E toward saddle 30 until external thread 41 of coupling member 42 touches coupling region 35 of saddle 30 and can be screwed into internal thread 38 of coupling region 35 of saddle 30.

Figure 9C:
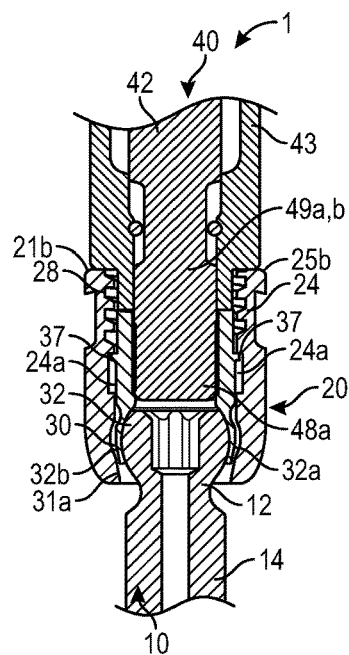

FIG. 9c shows tool 40 now coupled in a rotationally fixed manner to tulip 20. Screw 10 is connected to tulip 20 via screw head 12, which is situated in receiving region 32 of the saddle. The rotationally fixed connection of tool 40 to tulip 20 enables the rotational movement of coupling member 42 as it is being screwed into internal thread 38 of saddle 30 to be converted into an axial movement of saddle 30 in direction of insertion E. Saddle 30 is thereby moved, as is shown in FIG. 9c, out of locked position 23b in insertion direction E into released position 23a. In released position 23a of saddle 30, tulip 20 has a maximum inner diameter DImax in a plane 23c that coincides with receiving opening 32b of saddle 30. The maximum inner diameter DImax of tulip 20 in plane 23c, which is defined by released position 23a, permits a maximum expansion of receiving opening 32b of receiving region 32 of saddle 30 in a transverse direction Q to a released expansion DF, which is greater than maximum width BK of screw head 12.

Figure 9D:
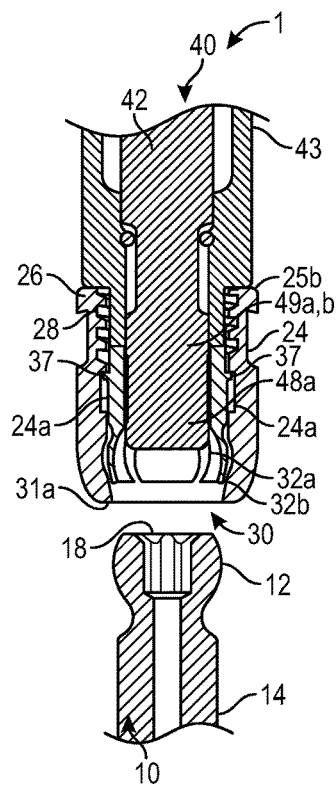

When, as shown in FIG. 9d, screw 10 and tool 40 are then moved away from one another, screw head 12 can be disengaged from receiving region 32 of saddle 30. This is possible because tool 40 fixes the position of saddle 30 in released position 23a.

If the steps illustrated in FIGS. 9a to 9d are carried out in reverse order, then screw 10 can be connected to head piece 2 by applying a small amount of force in the axial direction.

LIST OF REFERENCE SIGNS 1 instrument set
2 head piece
10 screw
12 screw head
14 shaft
14a cannula
14b window
15a first head region
15b second head region
16a first shaft region
16b second shaft region
17a first thread
17b second thread
18 recess
BK maximum width of screw head
bK second width of screw head
20 tulip
21b first insertion opening
21b second insertion opening
22 interior region
23a released position
23b locked position
23c plane
24 wall
24a recess
24b first stop region
24c second stop region
25a first end region
25b second end region
26 edge region
27 indentation
28 locking device
DImin minimum inner diameter
DImax maximum inner diameter
30 saddle
31a first end region
31b second end region
32 receiving region
32a wall
32b receiving opening
33 slot
33a material bridge
35 coupling region
37 projection
37a first stop surface
37b second stop surface 38 internal thread
39 recess
L1 first position
L2 second position
DS locked expansion
DF released expansion
40 tool
41 external thread
42 coupling member
43 holding grip
43a window
43b grooves
44 interior space
45a first end region
45b second end region
46 twist grip
47a first end position
47b second end position
48a first holding grip end region
48b second holding grip end region
49 locking device
49a first projection
49b second projection
50 set screw
60 screwdriver
100 rod system
101 rod
E insertion direction
Q transverse direction
L longitudinal axis of tulip
L' longitudinal axis of saddle
A longitudinal axis of coupling member

The invention claimed is:

1. An instrument set for connecting vertebral bodies, comprising a screw which has a screw head and a shaft and is screwable into a pedicle, a head piece which is connectable polyaxially to the screw for coupling to a rod system and which has a sleeve-shaped tulip having a first insertion opening for insertion of the screw head in an insertion direction,
and a tool,
wherein the head piece has a saddle in the interior region of the tulip, the saddle is situated rotationally fixed in the tulip and has a receiving region for receiving the screw head in a first end region that faces the first insertion opening and a coupling region to be coupled to a coupling member of the tool in a second end region opposite the receiving region, and the saddle is movable between a released position, which is reachable by inserting the screw head, and a locked position, which is reachable by moving the screw head out of the released position in the direction opposite the insertion direction,
wherein when the saddle is in the locked position, the screw head held in the receiving region is not to be disengaged from the receiving region, and
wherein when the coupling member of the tool is coupled to the coupling region of the saddle, the saddle is to be fixed in the released position that enables the release of the screw head from the receiving region such that the head piece and the screw are to be separated,
wherein the coupling member is rotatable around a longitudinal axis and the rotational movement of the coupling member is converted to an axial movement of the saddle between the released position and the locked position without rotation of the saddle,
and wherein the coupling region of the saddle has an internal thread.

2. The instrument set according to claim 1, wherein the receiving region, which is delimited by a wall and has a receiving opening for insertion of the screw head, is reversibly deformable in a transverse direction that extends perpendicular to a longitudinal axis of the tulip.

3. The instrument set according to claim 2, wherein the receiving region is elastically deformable.

4. The instrument set according to claim 2, wherein the wall of the receiving region is subdivided by at least two slots and/or windows into at least two separate sections.

5. The instrument set according to claim 4, wherein the slots and/or windows are embodied as T-shaped.

6. The instrument set according to claim 2, wherein, at least in the locked position, a wall of the tulip limits a deformation of the receiving region in the transverse direction.

7. The instrument set according to claim 1, wherein the screw head, in a first head region, has a maximum width in a direction perpendicular to the shaft, and in a second head region located between the first head region and the shaft, has a second width in the direction perpendicular to the shaft, the second width being smaller than the maximum width.

8. The instrument set according to claim 7, wherein in the locked position of the saddle, an inner wall of the tulip limits a maximum expansion of the receiving opening that can be achieved by a deformation in the transverse direction to a locked expansion, which is smaller than the maximum width and is greater than or equal to the second width of the screw head, and in the released position of the saddle, the wall of the tulip permits a maximum expansion of the receiving opening that can be achieved by a deformation in the transverse direction to a released expansion, which is greater than the maximum width of the screw head.

9. The instrument set according to claim 1, wherein the tulip and the saddle are separably connected to one another.

10. The instrument set according to claim 1, wherein the tulip, in a second end region opposite the first insertion opening, has a second insertion opening with an edge region, in which two diametrically opposing indentations for receiving a rod of the rod system are formed.

11. The instrument set according to claim 10, wherein the saddle, in a second end region which is located in the direction of the second insertion opening of the tulip, has a recess extending diametrically through the saddle and designed for receiving the rod that is positioned in the indentations in the edge region of the tulip.

12. The instrument set according to claim 1, wherein the tulip has, in its second end region, a locking device for fixing the rod.

13. The instrument set according to claim 1, wherein the tool has a holding grip having a hollow interior space, wherein the coupling member is situated at least partially within the interior space.

14. The instrument set according to claim 13, wherein the coupling member is embodied as cylindrical.

15. The instrument set according to claim 13, wherein the coupling member has a twist grip in the second end region of the tool opposite the first end region of the tool.

16. The instrument set according to claim 13, wherein the tool has a locking device with which the holding grip can be connected to the tulip in a rotationally fixed manner.

17. The instrument set according to claim 13, wherein the coupling member can be displaced in relation to the holding grip in the axial direction between a first end position and a second end position.

18. The instrument set according to claim 1, wherein the coupling member of the tool has an external thread in a first end region for screwing to the internal thread of the coupling region.

19. The instrument set according to claim 1, wherein the screw is solid or cannulated and/or fenestrated.

20. The instrument set according to claim 1, wherein the screw has a first thread having a first thread pitch and a second thread having a second thread pitch, and the first and second thread pitches are the same or different.

21. The instrument set according to claim 20, wherein the first thread pitch and the second thread pitch are the same, and the two threads are arranged along the shaft of the screw in such a way that the screw is double-threaded in a second shaft region adjacent to the screw head, and is single-threaded in a first shaft region extending away from the second shaft region opposite the screw head.

22. The instrument set according to claim 1, wherein the screw head has a recess for receiving a screwdriver.

23. An instrument set for connecting vertebral bodies, comprising a screw which has a screw head and a shaft and is screwable into a pedicle, a head piece which is connectable polyaxially to the screw for coupling to a rod system and which has a sleeve-shaped tulip having a first insertion opening for insertion of the screw head in an insertion direction, and a tool,
wherein the head piece has a saddle in the interior region of the tulip, the saddle is situated rotationally fixed in the tulip and has a receiving region for receiving the screw head in a first end region that faces the first insertion opening and a coupling region to be coupled to a coupling member of the tool in a second end region opposite the receiving region, and the saddle is movable between a released position, which is reachable by inserting the screw head, and a locked position, which is reachable by moving the screw head out of the released position in the direction opposite the insertion direction,
wherein when the saddle is in the locked position, the screw head held in the receiving region is not to be disengaged from the receiving region, and
wherein when the coupling member of the tool is coupled to the coupling region of the saddle, the saddle is to be fixed in the released position that enables the release of the screw head from the receiving region such that the head piece and the screw are to be separated,
wherein the coupling member is rotatable around a longitudinal axis and the rotational movement of the coupling member is converted to an axial movement of the saddle between the released position and the locked position without rotation of the saddle,
wherein an inner diameter of the tulip is minimal at the first insertion opening, and an inner diameter of the tulip is maximal in a plane defined by the receiving opening of the saddle in the released position.

24. An instrument set for connecting vertebral bodies, comprising a screw which has a screw head and a shaft and is screwable into a pedicle, a head piece which is connectable polyaxially to the screw for coupling to a rod system and which has a sleeve-shaped tulip having a first insertion opening for insertion of the screw head in an insertion direction, and a tool,
wherein the head piece has a saddle in the interior region of the tulip, the saddle is situated rotationally fixed in the tulip and has a receiving region for receiving the screw head in a first end region that faces the first insertion opening and a coupling region to be coupled to a coupling member of the tool in a second end region opposite the receiving region, and the saddle is movable between a released position, which is reachable by inserting the screw head, and a locked position, which is reachable by moving the screw head out of the released position in the direction opposite the insertion direction,
wherein when the saddle is in the locked position, the screw head held in the receiving region is not to be disengaged from the receiving region, and
wherein when the coupling member of the tool is coupled to the coupling region of the saddle, the saddle is to be fixed in the released position that enables the release of the screw head from the receiving region such that the head piece and the screw are to be separated,
wherein the coupling member is rotatable around a longitudinal axis and the rotational movement of the coupling member is converted to an axial movement of the saddle between the released position and the locked position without rotation of the saddle,
wherein the axial movement of the saddle in the tulip is limited between a first position and a second position, wherein the first position coincides with the released position, wherein the saddle has at least one projection between the receiving region and the coupling region, projecting toward a wall of the tulip and engaging in a recess that is formed in the wall of the tulip, wherein the projection, which abuts against first and second stop regions that delimit the recess in the axial direction when the saddle is moved axially, limits the movement of the saddle between the first position and the second position.

25. A method for inserting a screw and a head piece of the instrument set according to claim 1 into a vertebral body, the method comprising:
screwing the screw into the vertebral body;
coupling the tool to the tulip of the head piece in a rotationally fixed manner;
coupling the coupling member of the tool with the coupling region of the saddle;
rotating the coupling member wherein the rotational movement of the coupling member is converted into an axial movement of the saddle such that the saddle is moved into the released position;
fixing the saddle in the released position by the tool;
inserting the screw head into the receiving portion of the saddle; and
rotating the coupling member such that an axial movement of the saddle due to the rotation moves the saddle into the locked position.

26. A method for removing a head piece from a screw that is screwed into a vertebral body, wherein the screw has a screw head and a shaft and is screwable into a pedicle, wherein the head piece is connectable polyaxially to the screw for coupling to a rod system and which has a sleeve-shaped tulip having a first insertion opening for insertion of the screw head in an insertion direction,
and a tool,
wherein the head piece has a saddle in the interior region of the tulip, the saddle is situated rotationally fixed in the tulip and has a receiving region for receiving the screw head in a first end region that faces the first insertion opening and a coupling region to be coupled to a coupling member of the tool in a second end region opposite the receiving region, and the saddle is movable between a released position, which is reachable by inserting the screw head, and a locked position, which is reachable by moving the screw head out of the released position in the direction opposite the insertion direction, wherein when the saddle is in the locked position, the screw head held in the receiving region is not to be disengaged from the receiving region, and wherein when the coupling member of the tool is coupled to the coupling region of the saddle, the saddle is to be fixed in the released position that enables the release of the screw head from the receiving region such that the head piece and the screw are to be separated, wherein the coupling member is rotatable around a longitudinal axis and the rotational movement of the coupling member is converted to an axial movement of the saddle between the released position and the locked position without rotation of the saddle, wherein the method comprises:
- coupling the tool with the tulip of the head piece in a rotationally fixed manner;
- coupling the coupling member of the tool with the coupling region of the saddle;
- rotating the coupling member wherein the rotational movement of the coupling member is converted into an axial movement of the saddle such that the saddle is moved into the released position; and
- disengaging the head piece from the screw head.

* * * * *